United States Patent [19]

Mathiprakasam

[11] Patent Number: 4,601,587

[45] Date of Patent: Jul. 22, 1986

[54] DEVICE AND METHOD FOR DETERMINING FREEZING POINTS

[75] Inventor: Balakrishnan Mathiprakasam, Overland Park, Kans.

[73] Assignee: Midwest Research Institute, Kansas City, Mo.

[21] Appl. No.: 534,352

[22] Filed: Sep. 21, 1983

[51] Int. Cl.⁴ .......................................... G01N 25/02
[52] U.S. Cl. ........................................ 374/25; 374/16
[58] Field of Search ...................... 374/16, 25, 26, 31, 374/33, 34, 13; 136/200, 224

[56] References Cited

U.S. PATENT DOCUMENTS

| | | | |
|---|---|---|---|
| 3,250,115 | 5/1966 | Donnell | 374/25 |
| 3,267,728 | 8/1966 | Solomons | 73/190 |
| 3,319,457 | 5/1967 | Leone | 374/20 |
| 3,360,993 | 1/1968 | MacMillan | 73/361 |
| 3,504,525 | 4/1979 | Ishii | 73/17 |
| 3,518,838 | 7/1970 | Newton | 136/200 |
| 3,564,900 | 2/1971 | Andre et al. | 73/17 |
| 3,667,280 | 6/1972 | Simpson | 73/17 |
| 3,695,093 | 10/1972 | Hummel et al. | 73/17 |
| 4,383,770 | 5/1983 | Boschung et al. | 374/25 |

FOREIGN PATENT DOCUMENTS 1176907 4/1968 United Kingdom ............. 1/25

OTHER PUBLICATIONS

"Thermal Analysis", by T. Daniels, Kogan Page Ltd., 1973.
"Determination of the Purity of Hydrocarbons by Measurement of Freezing Points", A. R. Glascow, Jr. et al., U.S. Department of Commerce, National Bureau of Standards, 1945.

Primary Examiner—Steven L. Stephan
Assistant Examiner—David R. Schuster
Attorney, Agent, or Firm—Merchant, Gould, Smith, Edell, Welter, Schmidt

[57] ABSTRACT

A freezing point method and device (10) are disclosed. The method and device pertain to an inflection point technique for determining the freezing points of mixtures. In both the method and device (10), the mixture is cooled to a point below its anticipated freezing point and then warmed at a substantially linear rate. During the warming process, the rate of increase of temperature of the mixture is monitored by, for example, thermocouple (28) with the thermocouple output signal being amplified and differentiated by a differentiator (42). The rate of increase of temperature data are analyzed and a peak rate of increase of temperature is identified. In the preferred device (10) a computer (22) is utilized to analyze the rate of increase of temperature data following the warming process. Once the maximum rate of increase of temperature is identified, the corresponding temperature of the mixture is located and earmarked as being substantially equal to the freezing point of the mixture. In a preferred device (10), the computer (22), in addition to collecting the temperature and rate of change of temperature data, controls a programmable power supply (14) to provide a predetermined amount of cooling and warming current to thermoelectric modules (56).

50 Claims, 10 Drawing Figures

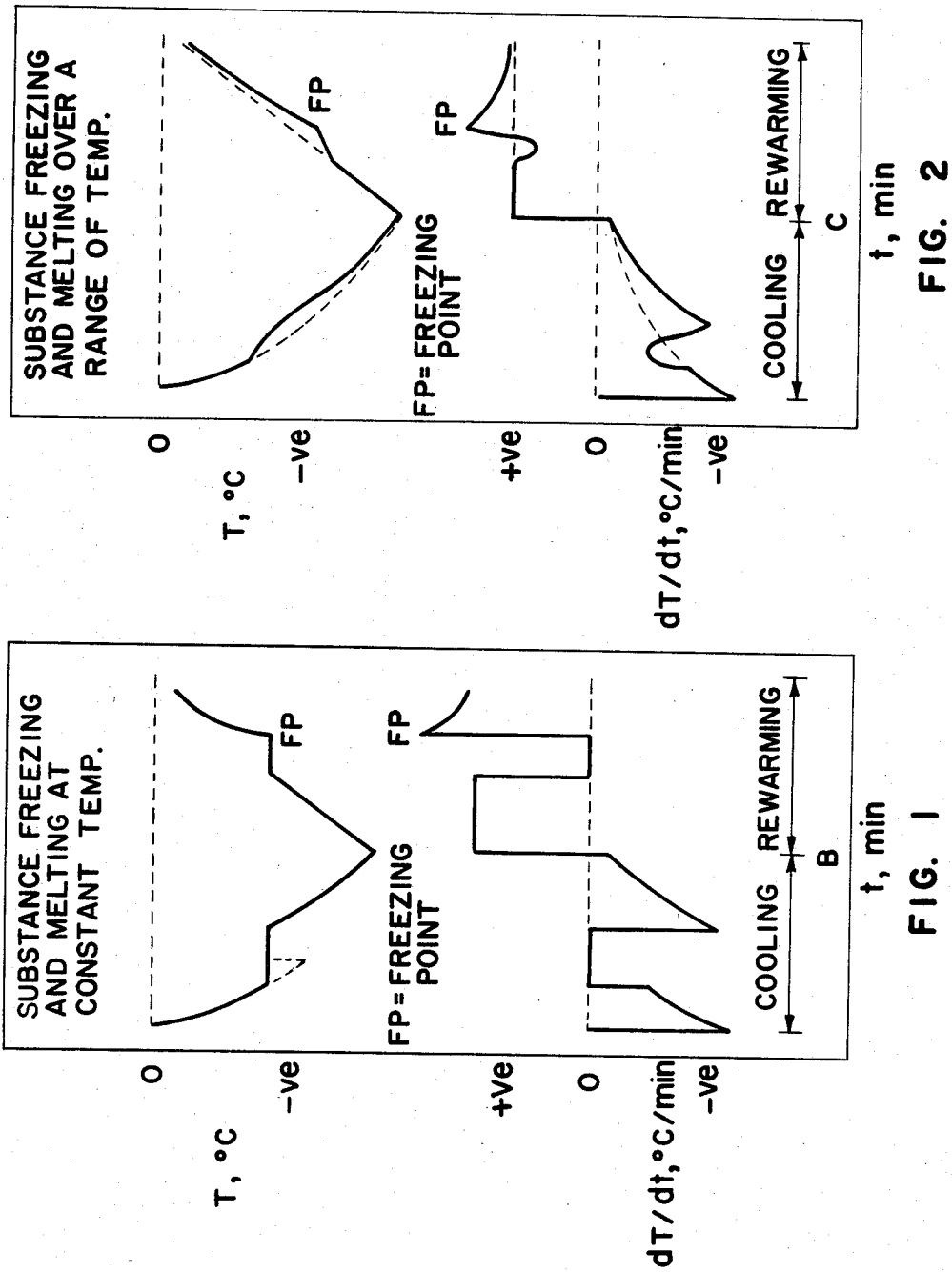

DEVICE AND METHOD FOR DETERMINING FREEZING POINTS

FIELD OF THE INVENTION

The present invention relates generally to devices and methods for determining freezing points, and more particularly to a method and device for determining the freezing points of mixtures which employ the inflection point principle.

BACKGROUND OF THE INVENTION

This invention was made with Government support under contract NAS 3-22543 awarded by NASA. The Government has certain rights in this invention.

It has long been appreciated that a key property of any substance is the substance's freezing point. The property is used to characterize substances in a variety of fields, including manufacturing process control and for aviation fuel characterization as further discussed below.

As is well known, when a substance freezes a crystalline structure develops in the substance. Although, strictly speaking, the freezing point of a substance is the temperature at which its solid and liquid phases are in equilibrium, the freezing point of a substance is herein defined as the highest temperature at which the aforementioned crystalline structure is present. More particularly, the present invention determines the freezing point on the basis that it is the highest temperature at which such crystals exist as the substance is being warmed from a temperature sufficiently below the anticipated freezing point to a temperature above the anticipated freezing point.

The freezing point of an element or single compound, a substance having a single species, will be more easily understood with reference to FIG. 1. FIG. 1 shows a temperature versus time plot for a typical single-species substance which is cooled and then warmed. With the exception of the holding period between the cooling and heating processes, it is assumed that heat is withdrawn at substantially a constant net rate during cooling and added at substantially a constant net rate during warming. The substance is first cooled to below its freezing point and then warmed to a temperature above its freezing point. Initially, as the substance is being cooled, the substance releases "sensible heat" and the temperature of the substance decreases as heat is withdrawn from the substance. If the substance is quiescent and if seed crystals are not present, the substance may supercool or under-cool as shown in dashed line in FIG. 1. The temperature of the substance plateaus when latent heat of solidification of the substance is released and the sensible heat of the substance remains substantially constant. Latent heat is released due to the nature of the formation of crystals within the substance as it freezes. Once the substance is frozen, the heat that is withdrawn may again be characterized as sensible heat and the temperature of the substance decreases. Furthermore, since the substance consists of a single species, once the substance is frozen it assumes a solid form.

Upon warming of the frozen single-species substance, the solid substance absorbs sensible heat and its temperature increases until another plateau is reached. For a period of time, latent heat of fusion (equal to the latent heat of solidification) is absorbed by the substance as the crystalline structure diminishes. Ultimately, the temperature rises quickly upward as the last of the latent heat is absorbed and the heat energy being supplied to the substance is utilized solely to raise the substance's sensible heat. To state the definition of freezing point in somewhat different terms, the freezing point of the substance is herein defined as the temperature of the substance at which the absorbed heat fails to possess a latent heat component. That is, the freezing point is substantially equal to the temperature at which the temperature vs. time curve suddenly rises following the latent heat absorption plateau. The point where the sudden temperature rise occurs is an "inflection point" of the temperature vs. time plot, the inflection point being the point at which the maximum rate of change of temperature occurs.

The freezing point of a substance having several species, i.e. a mixture, may be similarly defined. FIG. 2 shows a temperature vs. time plot for a typical mixture. As the mixture is cooled, sensible heat is released from the mixture and its temperature decreases. When one of the species begins to freeze, the heat that is withdrawn from the substance is partially sensible heat and partially latent heat, the latter being drawn from the freezing species. Thus, the temperature of the mixture drops off less rapidly than it did when only sensible heat was being withdrawn from the mixture. As the temperature continues to decrease, additional species of the hypothetical mixture begin to freeze and a noticeable plateau may exist, albeit the plateau effect is less pronounced for mixtures than it is for single-species substances, the latter's characteristics being shown in FIG. 1. Eventually, all or most of the species within the mixture freeze and the temperature decreases more rapidly, primarily sensible heat being released by the substance at this point.

Upon rewarming of the mixture, initially sensible heat alone is absorbed but soon latent heat is also being absorbed by the mixture as the various species begin to melt. When the species having the highest freezing point melts, i.e., when the last crystals within the mixture dissipate, the temperature of the mixture upturns somewhat more rapidly. This effect, discussed above with reference to single-species substances, arises because all of the heat that is "pumped" to the substance is sensible heat following the latent heat supply. The relatively sudden rate of increase in the temperature of the mixture signals the presence of the freezing point of the mixture, by the definition of freezing point adopted herein. As in the single-species case discussed above, the point at which the maximum rate of increase of temperature of the mixture occurs, the "inflection point," is the freezing point of the mixture. The first derivative of temperature with respect to time, $dT/dt$, is plotted versus time in FIG. 2. The temperature at which the peak rate of increase of temperature occurs is substantially equal to the freezing point of the mixture, by definition.

It should be emphasized that the freezing points of the single-species and multi-species substances can also be defined with reference to the cooling sides of the plots discussed above. That is, the freezing point of a substance can also be defined as the temperature at which crystals first begin to appear as opposed to the temperature at which the crystals disappear during heating. Supercooling of the substance must be avoided or accounted for, however, if the freezing point is determined during cooling.

Several methods and devices have been developed to measure freezing points of single-species and multi-species substances. The many techniques can generally be grouped into three categories: thermal techniques, optical techniques and "other" techniques.

Optical techniques have been employed to determine phase transition temperatures. At a phase transition, optical properties change, and specifically transparency at various wavelengths, x-ray absorption and index of refraction properties may change from the properties of the substance when a phase transition is occurring.

"Other" techniques for determing freezing points, exclusive of optical and thermal techniques, include analysis of the properties of the individual components of the substance, and measurement of magnetic permeability, electrical resistivity, density and viscosity.

Thermal techniques comprise one of the broad categories of the various freezing point determination techniques. One of the thermal methods employs the inflection behavior of the temperature vs. time curve for a substance, and the present invention is of the inflection point type. Generally, thermal methods measure the change in specific heat or heat capacity of a substance as it is being cooled or warmed to locate the plateau where latent heat is being absorbed or desorbed. Thermal methods include adiabatic calorimetry, thermal relaxation calorimetry, differential scanning calorimetry, differential thermal analysis, and inflection point techniques, the present invention being of the latter type.

Adiabatic calorimetry is possibly the most relevant calorimetry technique to the present invention. One of the thermal methods for determining physical properties of substances, adiabatic calorimetry is usually used for analyzing pure or single-species substances, and sometimes used for substances that have small amounts of impurity. The device is termed adiabatic due to the efforts to minimize heat transfer out of the "system." As described in a publication entitled *Thermal Analysis*, by T. Daniels, Anchor Press, Ltd., 1973, "programmed heating" is used to increase the temperature of the substance at some predetermined rate. A plateau is readily observable at the melting point of the substance, since pure or nearly pure substances possess very distinct changes between latent heat absorption and sensible heat absorption, with a sharp increase in temperature occuring when all of the substance has changed from the solid to the liquid phase.

As contrasted with adiabatic calorimetry, the present invention pertains to inflection point techniques for determining the freezing point of a substance. Inflection point techniques are very desirable primarily because of their relative simplicity, accuracy, repeatability, and direct dependence on a well-understood physical phenomenon, the formation or destruction of crystal lattices during a phase transition. As further constrasted with adiabatic calorimetry, the present invention is particularly directed to determining the freezing point of a multi-species substance, i.e., a mixture.

As described with reference to FIGS. 1 and 2, phase transitions occur both as a substance is cooled below its freezing point and as the substance is rewarmed to a temperature above its freezing point. Inflection point techniques can be used to determine either phase transition. In fact, U.S. Pat. No. 3,695,093, issued to Hummel et al., and U.S. Pat. No. 4,383,770, issued to Boschung et al., disclose devices which determine the freezing point of a substance based on a measurement of the rate of decrease of temperature of the substance during cooling. It is perceived, however, that super or undercooling presents a problem on the cooling side of the temperature vs. time plot. Thus, inflection point techniques that operate on data collected during the cooling process are inherently prone to complication.

In contrast to the Bochung and Hummel patents discussed above, U.S. Pat. No. 3,667,280, issued to S. W. Simpson, teaches an inflection point technique that operates on the heating or rewarming side of the curve. Simpson discloses cooling a sample until a noticeable plateau in the temperature vs. time plot occurs; warming the sample by placing the frozen sample in an insulated container, e.g. an insulated cup, in a warming environment; measuring the temperature of the sample as it is rewarming; differentiating the temperature to determine $dT/dt$ vs. time; continuing to warm the sample until a peak in the time differential of the temperature occurs; and recording the temperature of the sample at which the peak occurs. The sample is warmed quite slowly in the Simpson technique, between 2° Farenheit and 4° Farenheit per minute being preferred. In fact, the temperature of the substance inherently increases at an exponentially decaying rate in the Simpson technique, quite rapidly initially but much more slowly as the temperature of the sample nears room temperature.

It is perceived that the Simpson technique suffers from at least two major disadvantages: first, since the temperature increases quite slowly near room temperature (temperature of the warming environment), the output signal from the differentiator for substances with freezing points near room temperature is fairly unrecognizable, especially for mixtures that have many components having a wide spectrum of freezing points. That is, under the Simpson technique, for a mixture having a freezing point somewhat near room temperature, the output signal from a temperature differentiator at the freezing point is insufficiently distinctive. This is particularly true for mixtures such as a few aviation fuels which have freezing points near room temperature. Secondly, since the rewarming rate is not constant but varies during the rewarming process, the error in measured reading becomes a function of instantaneous rewarming rate at the time of approaching the freezing point. Therefore it is very difficult to estimate the error involved, depending upon the nature of the substance, the error could be significant.

Furthermore, a test according to the Simpson technique, with apparently a 2° Farenheit to 4° Farenheit average increase in temperature per minute, can take a considerably long period of time. When many substances must be tested, such a protracted procedure is burdensome.

The present invention is directed to the shortcomings of the inflection point techniques discussed above. Potential complications due to super or undercooling are avoided; the test consumes a fairly small amount of time; the error, if any, is independent of the freezing point and not prohibitively large for substances having extremely low freezing points, e.g., minus 60° Centigrade; and if the freezing point is near room temperature, the peak rate of increase of temperature is clearly discernable with a standard means for differentiating the temperature vs. time data. Furthermore, a freezing point measuring instrument according to the present invention can be made portable and automated for convenient field use.

SUMMARY OF THE INVENTION

The present invention is a device and method for determining the freezing point of a mixture. The method according to the present invention includes the following steps:

(a) cooling the mixture to a temperature less than its anticipated freezing point;

(b) controllably warming the mixture by actively controlling a net heat transfer thereto to increase the temperature of the mixture at a substantially constant or linear rate during that time when the mixture is not undergoing a phase change;

(c) identifying an instant of time when a peak rate of increase of temperature of the mixture occurs; and (d) determining the temperature of the mixture that existed at said instant of time, wherein this temperature is substantially equal to the freezing point of the mixture.

A preferred embodiment of the method includes thermoelectric warming and cooling. The "identifying" step discussed above comprises several sub-steps in a preferred embodiment:

(a) measuring the temperature of the mixture during the warming step;

(b) determining a rate of increase of temperature of the mixture during the warming step; and (c) identifying the peak rate of increase of temperature of the mixture that occurred during the warming step.

The method following the principles of the present invention is particularly advantageously applied to determining the freezing point of hydrocarbon mixtures and in that case the warming step includes increasing the temperature of the hydrocarbon mixture at a constant rate between approximately 20 and 25 degrees centigrade. Aviation fuels, one "class" of hydrocarbon mixtures, are accurately tested by the method herein described and in a time-efficient manner. The warming rate of 20 to 25 degrees centigrade have been found to be particularly useful in the testing of aviation fuels.

An additional step in a preferred embodiment of the method includes holding or maintaining the temperature of the mixture at a temperature below the mixture's anticipated freezing point for a predetermined period of time. This step tends to stabilize the mixture and leads to more accurate results.

A preferred method further includes electronic means for analyzing the rate of change of temperature data to identify the peak rate of change of temperature that occurred during the warming step.

In addition to the method discussed above, the present invention includes a device for determining the freezing point of a mixture. Such a device includes:

(a) means for cooling the mixture to a temperature less than its anticipated freezing point, the cooling means being in thermal communication with the mixture;

(b) means for controllably warming the mixture by actively controlling a net heat transfer thereto to increase the temperature of the mixture at a substantially constant rate during that time when the mixture is not undergoing a phase change, the warming means being in thermal communication with the mixture;

(c) means for measuring the temperature of the mixture, the temperature measuring means being in operative proximity of the mixture;

(d) rate sensing means operatively disposed to monitor the mixture for providing a rate signal indicative of the rate of change of temperature of the mixture; and (e) means operatively connected to the temperature measuring means and to the rate sensing means for determining an instant of time when the rate of increase of temperature attains a maximum and for providing a freezing point test output signal indicative of the temperature of the mixture at the instant of time, wherein this temperature is substantially equal to the freezing point of the mixture.

As outlined with respect to the method discussed above, the device according to the present invention preferably includes means for thermo-electrically warming and cooling the mixture under test.

A preferred device further includes temperature measuring means which provides first and second temperature signals, the signals being indicative of the temperature of the mixture, with the first temperature signal being received by the rate sensing means and the second temperature signal being received by the instant of time determining means. The rate sensing means is preferably an analog differentiator, the temperature signals being analog in nature, and the instant of time determining means is preferably a digital computer supplied with an analog interface for effective communication with the analog devices discussed above.

The preferred temperature measuring means is a hypodermic type thermocouple.

Also, and in the case of the method discussed above, the device is quite advantageously applied to hydrocarbon mixtures and in that case the constant rate of warming is preferably between approximately 20 and 25 degrees centigrade per minute.

Similarly, as in the case of the method discussed above, a preferred device includes means for maintaining or holding the temperature of the mixture at a temperature below the anticipated freezing point of the mixture. Such an addition to the device leads to more accurate results. The temperature holding or maintaining means preferably include a thermoelectric element or module.

The device according to the present invention is preferably applied to measuring the freezing points of hydrocarbon mixtures, and more particularly has been found very useful in the measurement of freezing points of aviation fuels.

BRIEF DESCRIPTION OF THE FIGURES

FIG. 1 is a temperature vs. time plot for a typical single-species substance which is cooled and then warmed.

FIG. 2 is a temperature vs. time plot for a typical mixture which is cooled and then warmed; FIG. 2 also shows a plot of the rate of change of temperature vs. time for the typical mixture.

DETAILED DESCRIPTION OF THE INVENTION

Figure 3:
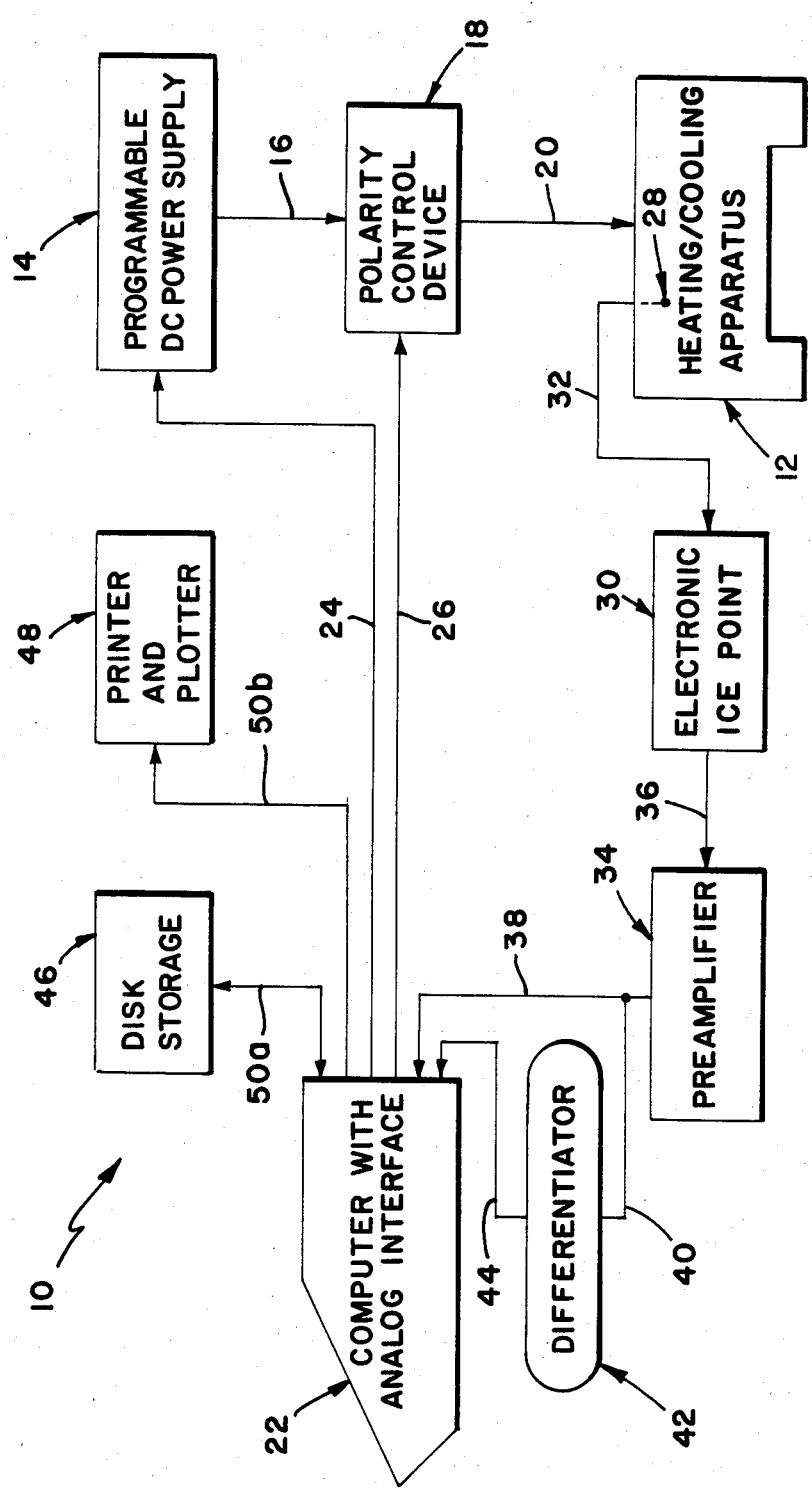
FIG. 3 is a schematic representation of a freezing point device constructed according to the principles of the present invention.

Referring now to the drawings wherein like reference numerals denote like elements throughout the several views, FIG. 3 illustrates, in schematic, a freezing point measuring device 10 constructed according to the principles of the present invention. A heating/cooling apparatus 12 houses a sample cell 54 and thermoelectric modules 56, as shown and described with reference to FIG. 4 below. It is well known to those skilled in the art of refrigeration, or more generally "heat pumping," that various cooling systems could be used in lieu of thermoelectric cooling, but the latter is preferred for reasons that are presented below. The thermoelectric modules 56 of the heating/cooling apparatus 12 are powered by a programmable DC power supply 14 which supplies the appropriate amount of direct current through first conductor 16, polarity control device 18 and second conductor 20 to the heating/cooling apparatus 12. Clearly, the first and second conductors, 16 and 20 respectively, are comprised of more than a single electrically-conductive wire, but they are illustrated as such for the sake of clarity.

The polarity control device 18 is preferably a relay and it serves to transform the unidirectional current in the first conductor 16 to one of either two directions or polarities in the second conductor 20 so that current can be directed in one of two directions through the thermoelectric modules 56 to effect cooling or heating as appropriate.

As mentioned above, the output of the programmable DC power supply 14 is a unidirectional DC current in the first conductor 16. The magnitude of the current is controlled by a computer 22, the computer 22 providing an analog control voltage signal on a third conductor 24 interconnecting the computer 22 and the programmable DC power supply 14. The computer 22 preferably includes an analog interface board (not shown) which includes a digital-to-analog converter so that a digital voltage from the central processor, e.g., a microprocessor, can be converted to an analog voltage on the third conductor 24 to control the amount of current issuing from the programmable DC power supply 14. Thus, the computer 22 controls the amount of current flowing through the thermoelectric modules by controlling the analog voltage on the third conductor 24, and the computer 22 controls the direction or polarity of current flow by controlling the "state" of the polarity control device 18.

The polarity control device 18 is preferably a relay, as noted earlier, and the amount of current or rather the presence or absence of current flowing through the relay's coil is provided by the computer 22 via a fourth conductor 26 interconnecting the computer 22 and the polarity control device 18. Clearly, the control signal on the fourth conductor 26 is in the nature of a binary signal, either being "on" or "off," and therefore this control signal can either be generated directly by the microprocessor, an amplified version of one its binary outputs, or the signal can be generated by a digital-to-analog converter and an amplifier. Those skilled in the art of electronic circuit design recognize that the programmable DC power supply 14 and the polarity control device 18 can be controlled by any number of means and the present invention is not limited to any particular type of control. In fact, it is not necessary that a computer be used for the control of and data collection from the heating/cooling apparatus 12, but a computer is preferred because of its programmability and the rapidity and preciseness with which it can calculate control signals and store temperature data.

As the sample is heated and cooled by the thermoelectric modules 56 within the heating/cooling apparatus 12, the temperature of the sample is preferably measured by a thermocouple 28 in thermal contact with, e.g., immersed within, the sample. The raw analog signal from the thermocouple 28 is transmitted to an electronic ice point 30 by fifth conductor 32. The electronic ice point 30 translates the raw thermocouple signal to an equivalent millivolt signal for further processing. Since the amplitude of the signal delivered by the electronic ice point 30 is typically too low to be processed by the analog-to-digital converters within a computer, a preamplifier 34, connected to the electronic ice point 30 by a sixth conductor 36, is used in the freezing point measuring device 10 to increase the ice point signal by a significant amount, e.g., two orders of magnitude.

Once the information from the thermocouple 28 is thus conditioned and amplified, it is presented to the computer 22 through the use of a seventh conductor 38, the signal carried by the seventh conductor 38 being directly related to the temperature of the sample in a predetermined fashion depending on the calibration of the thermocouple 28 as is well known in the art of thermocouple use. An eighth conductor 40 also receives the temperature signal provided by the preamplifier 34 to an analog differentiator 42. The differentiator 42 is of a type commonly used in the electronic design art, and it produces the derivative of the temperature signal with respect to time, i.e. $dT/dt$. Of course, the time derivative of the temperature signal could also be derived by the computer 22 through a programmed analysis of the temperature versus time data. The output of the differentiator 42 is carried by a ninth conductor 44 to the analog interface board (not shown) which may be considered a part of the computer 22.

The computer 22, as mentioned above, includes an analog interface board which allows the digital computer 22 to effectively communicate with analog devices including the programmable power supply 14, the differentiator 42 and the preamplifier 34. The computer 22 includes a keyboard (not shown) which allows it to be appropriately programmed for the test sequence as described below. The keyboard allows the individual supervising the test to input various parameters to the computer 22 to structure the test according to the characteristics of the substances being tested, among other factors. The computer 22 is also preferably connected to various peripheral devices, including a disk memory device 46 and a printer and plotter, collectively designated with the numeral 48. Conductors 50a and 50b interconnect the peripheral devices 46 and 48 to the computer 22, respectively. Again, as well known in the art of computer usage and design, the conductors 50a and 50b are preferably each a plurality of conductors in the form of a ribbon cable or the like although represented in schematic form in FIG. 3 as single lines. The printer/plotter 48 is used to display the results of the test. The temperature and rate of change of temperature data, collected and stored by the computer 22 during the test, can thus be plotted, and the freezing point can be printed following the test sequence.

It should be emphasized that although the freezing point measuring device 10 is preferably constructed as described above, there is a wide variety of possible designs for the hardware and software of such a system. In fact, it is not absolutely necessary that a computer be used as the controlling device, a hard-wired controller being a less desirable but adequate substitution for the computer 22. Additionally, the thermocouple 28 could be replaced by another temperature-measuring device such as a thermistor or the like.

Figure 4:
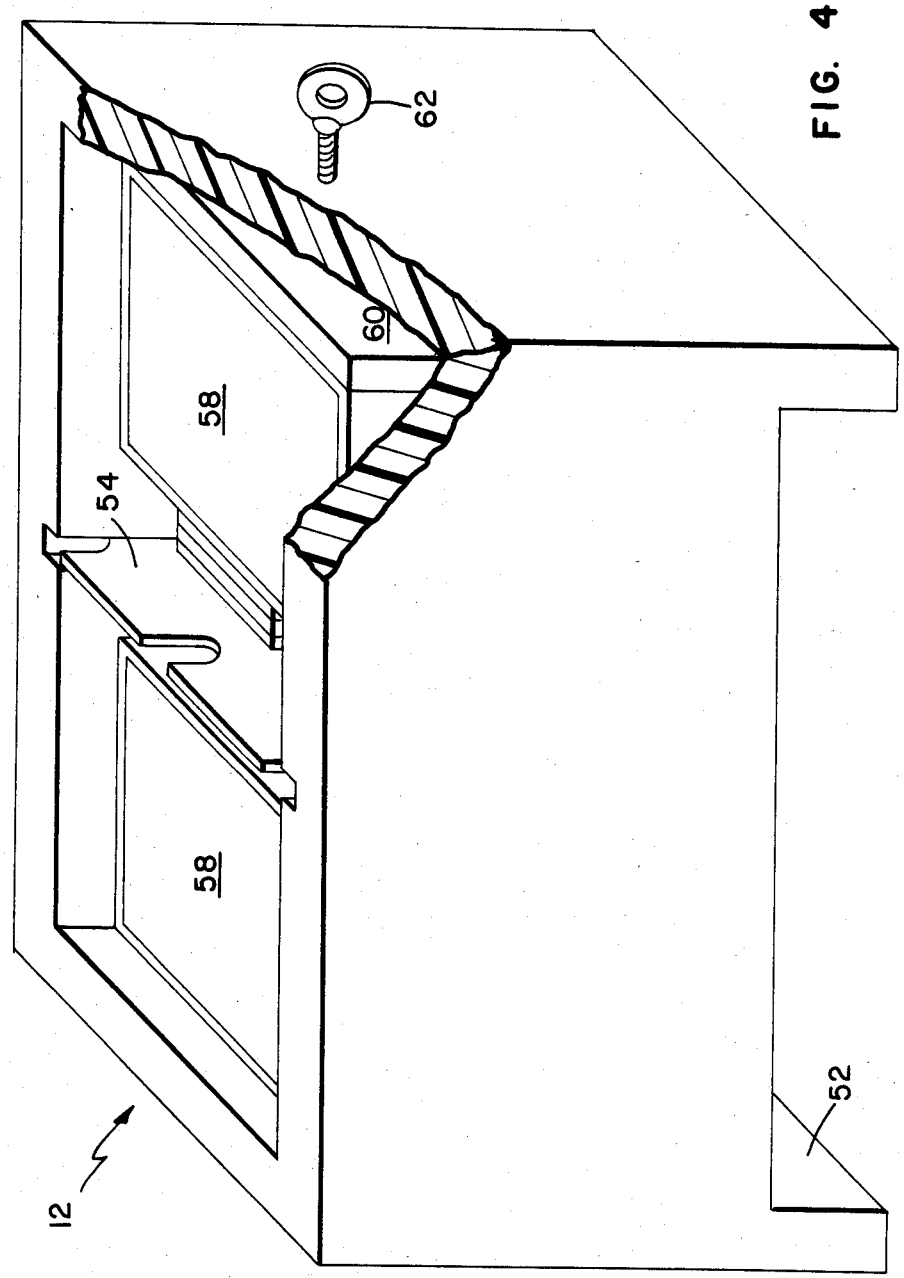
FIG. 4 is an isometric view of a thermoelectric unit which preferably is a component of the freezing point device shown in FIG. 3.

An isometric view of the heating/cooling apparatus 12 is shown in FIG. 4. A housing 52 contains the various components of the heating/cooling apparatus. The housing 52 is preferably fabricated from acrylic or the like using well-known techniques. A sample holder 54, substantially centrally located within the housing 52, forms a cavity which contains a small amount of the substance that is to be tested by the freezing point measuring device 10. The sample holder 54 is also preferably formed from acrylic: a thin, substantially planar piece of acrylic is milled to provide a thin, wafer-like gap for the sample, thus maximizing the surface area and minimizing thermal lag. It has been found that a 2.5 milliliter sample is preferred for the design of the heating/cooling device 12 as herein described. A larger sample size requires more powerful heaters/coolers and a smaller sample size fails to exhibit identifiable peak signals.

The sample holder 54 forms a small hole 56 at its topmost edge which admits the thermocouple 28 to the gap containing the sample so that the temperature of the sample can be measured during the test.

On either side of the substantially planar sample holder 54 is a thermoelectric module 56. In fact, in the preferred embodiment, the thermoelectric modules 56 form the sides of the volume which contains the sample. For the purpose of determining the freezing point of various aviation fuels, it has been found that three-stage thermoelectric modules are sufficient. Three-stage thermoelectric modules permit the sample to be cooled to a temperature of −60° Centigrade, cold enough for the testing of most aviation fuels. Such three-stage thermoelectric modules can presently be purchased from the manufacturers such as Melcor Materials Electronic Products Corporation of Trenton, New Jersey.

Ice baths 58 are in direct contact with the thermoelectric modules 56, each of the thermoelectric modules 56 being sandwiched between the sample holder 54 and one of the ice baths 58. The ice baths 58 are preferably simple boxes formed from thin metal sheet stock, e.g., brass sheet, and filled with a mixture of ice and water. The ice baths 58 supply heat energy to the thermoelectric modules 56 when heat energy is being "pumped" to the sample within the sample holder 54; and the ice baths 58 act as energy "sinks" during the time that heat energy is being pumped from the sample. The ice baths 58, the thermoelectric modules 56 and the sample holder 54 are preferably slidable within the housing 52 in a direction perpendicular to the substantially planar sample holder 54. The various components of the heating/cooling apparatus 12 are pressed into efficient heatconductive engagement by a pressure plate 60 which is likewise slidable within the housing 52 with the pressure plate 60 being engaged by a clamp screw 62 which threadedly engages one of the end walls of the housing 52. When the clamp screw 62 is appropriately turned about its longitudinal axis, pressure is applied by the clamp screw 62 to the pressure plate 60 which in turn distributes the stress and presses against the proximate ice bath 58, with the net effect being that the various components of the heating/cooling apparatus 12 are pressed into heat conductive contact to maximize the efficiency of the device and the time responsiveness of the sample as it is being cooled and rewarmed.

Figure 5:
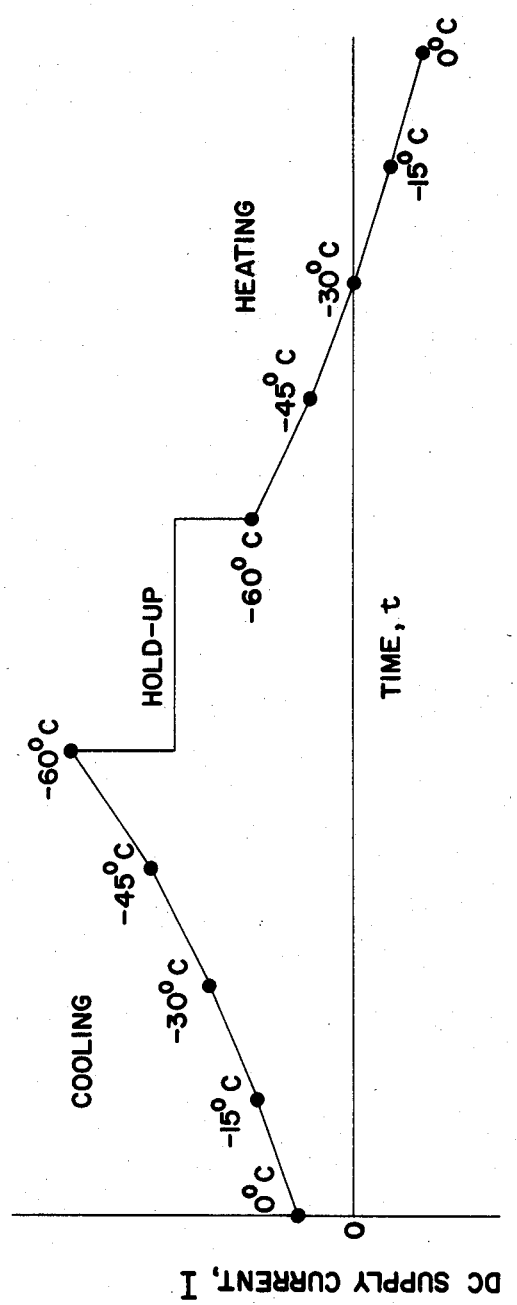
FIG. 5 is a representative plot of current vs. time supplied to the thermoelectric modules of the thermoelectric unit of FIG. 4 in order to linearly cool, hold, and then linearly warm the test substance.

The method of the present invention, and operation of the freezing point measuring device 10, an apparatus constructed and operated under the principles of the present invention, can be described with reference to FIGS. 5–10. FIG. 5 illustrates a typical plot of thermoelectric module current vs. time for freezing point determination test according to the present invention. As noted above, the freezing point of a substance, particularly a mixture, is optimally determined by linearly rewarming a frozen sample of the substance and detecting a peak rate of increase of temperature that occurs during the linear rewarming. The temperature of the substance at that peak rate of increase of temperature is herein defined as the freezing point of the substance being tested. The amount of current being supplied to the thermoelectric modules 56 by the programmable DC power supply 14 determines the rate of cooling or heating of the substance within the sample holder 54 of the heating/cooling apparatus 12. FIG. 5 shows a typical plot of current vs. time that is preferably supplied to the thermoelectric modules during the test. It should be noted that the amount of current that must be supplied to the thermoelectric modules 56 at any given instant of time is particularly a function of the type of thermoelectric modules and their efficiency. It is well known in the art of thermoelectric cooling and heating that a nonlinear current vs. time characteristic is generally required to effect linear cooling and heating in a non-adiabatic system. The parameters of the particular thermoelectric elements must be characterized according to well-known techniques; and following this straight-forward investigation a plot such as that illustrated in FIG. 5 can be generated and used in the control of the amount of current flowing through the thermoelectric modules. Following this procedure, any given cooling and rewarming pattern can be generated. A non-freezing substance having a heat capacity similar to the substances under test can be used to calibrate the system for linear rewarming. For example, iso-octane is preferably used as a calibration substance for aviation fuels.

According to the present invention, the substance is first cooled to a temperature less than its anticipated freezing point; preferably, the temperature is then held for a predetermined period of time to cause the substance to stabilize; the substance is then rewarmed at a linear rate, i.e., approximately 20° Centigrate to 25° Centigrate per minute for hydrocarbon mixtures; and the peak rate of increase of temperature indicates that the substance has reached its freezing point. As shown in FIG. 5, the current supplied to the thermoelectric modules 56 monotonically increases as the substance is cooled from, for example, 0° Centigrade to −60° Centigrade. Minus 60° Centigrade was chosen because it is below the anticipated freezing point of most of the aviation fuels for which the freezing point determining apparatus 10 is particularly advantageous. The temperature of the substance is then held constant by maintaining a constant current flow through the thermoelectric modules 56. Following the hold up period, the substance under test is substantially linearly rewarmed. The current supplied by the programmable DC power supply 14 is progressively reduced in order that a constant heat energy will be "pumped" to the sample by the thermoelectric modules 56. The temperature of the substance increases due to the heat input through the walls of the housing 52 of apparatus 12. Clearly, if the apparatus 12 were more or less thermally insulated from the atmosphere, the amount of current supplied to the thermoelectric modules 56 would vary from the characteristic shown in FIG. 5.

Finally, at some point in the rewarming process, the thermoelectric modules 56 will typically need to receive current in the reversed direction in order to warm it at a linear rate. For the three-stage Melcor thermoelectric modules 56 that have been utilized and for typical aviation fuels with a sample size of 2.5 cubic centimeters, the transition point occurs at approximately −30° Centigrade. At this transition point, the direction of DC current flowing through the thermoelectric modules 56 is reversed in order to cause heating of the sample by thermoelectric modules 56. The polarity control device 18, shown schematically in FIG. 3, switches the direction of current flow through the conductor 20 and is controlled by the computer 22. When the thermoelectric warming current becomes negligible, the state of the relay (not shown) within the polarity control device 18 is switched by the computer 22 so that the direction of current flow through the thermoelectric modules 56 reverses. In order to continue to heat the sample at a linear rate, progressively-increasing heating current is supplied to the thermoelectric module 56 as shown in FIG. 5.

Figure 6:
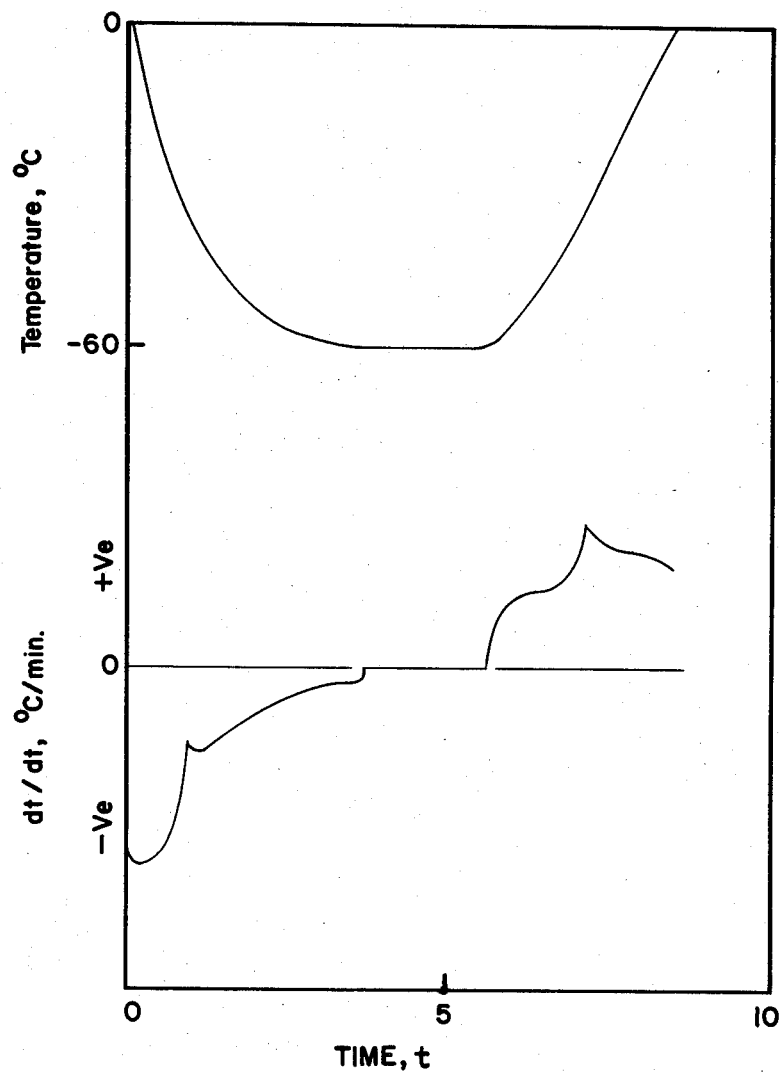
FIG. 6 shows a temperature vs. time plot for a mixture, the plot being generated by the freezing point device illustrated in FIG. 3 showing the sharp upturn in temperature upon complete melting that is particularly characteristic of the device when thermoelectric heaters are used.

FIG. 6 shows a representative plot of temperature vs. time for an aviation fuel test performed on the freezing point measuring device 10 using the current vs. time plot illustrated in FIG. 5. The computer 22 commands the power supply 14 to cause the thermoelectric modules 56 to cool the sample so that the temperature of the substance is automatically decreased until a "thermal event" occurs near the freezing point of the substance. The substance will oftentimes under or supercool to a temperature slightly below the plateau which is indicative of latent heat desorption. Once past the plateau, the temperature of the substance continues to drop until it reaches, for example, −60° Centigrade. The temperature is typically held at −60° Centigrade for two or three minutes and then the substance is rewarmed. Rewarming takes place at a constant (linear) rate, preferably approximately 20°-25° Centigrade per minute for aviation fuels which are types of hydrocarbon mixtures. The temperature of the substance follows the solid line during rewarming as shown in FIG. 6. A fairly sudden increase in temperature occurs at the freezing point since latent heat absorption ceases as can be seen from the dT/dt plot. The sudden increase in temperature at the freezing point is particularly emphasized by an open-loop control system in conjunction with the use of the thermoelectric modules 56 which are "commanded" to continue operating as if the substance were linearly reheating throughout the warming period when in fact the substance is undergoing a latent heat process so that when the last of the crystals dissipate during the rewarming, the temperature of the substance will upturn at a noticeable rate, making the peak rate of increase of temperature more easily identifiable. It should again be emphasized that a linear rewarming rate is particularly useful for mixtures since the rate of change of temperature for mixtures can be quite small at the inflection point. Maintaining a reasonably rapid rate of heat transfer throughout rewarming ensures that a noticeable inflection point will occur.

FIGS. 7–10 show a flow chart from which a computer program for the computer 22 can be written. A computer program following the flow chart herein described will cause the computer 22 and associated devices to automatically cool the sample at a prescribed rate during non-freezing periods; hold a minimum temperature for a predetermined length of time; and rewarm the substance at a preselected linear rate during non-thawing periods. Throughout the test, the computer 22 is instructed to input and record the temperature of the sample and the rate of change of temperature of the sample. It is abundantly clear to those skilled in the art of computer programming that the flow chart shown in FIGS. 7–10 is sufficiently instructive of the basic logic of the testing sequence to allow the straight forward writing of a corresponding computer program in any of a number of computer languages.

It should also be noted that open-loop control is the preferred method for linearly controlling the rewarming of the sample. That is, it has been found advantageous to calculate the amount of thermoelectric module current based on the running time and the preselected rewarming rate and not based on the temperature of the substance at any given time. A closed-loop system tends to be more complex and can cause instabilities of the temperature vs. time curve sufficient to be detected as "inflection points." However, the present invention contemplates any control technique that results in a substantially linear rewarming rate to determine freezing points by the inflection method. In a preferred embodiment, the computer 22 calculates the control signal for the programmable power supply 14 based on the state of a running clock and on a preselected rewarming rate, not on the actual temperature or rate of change of temperature of the substance.

Figure 7:
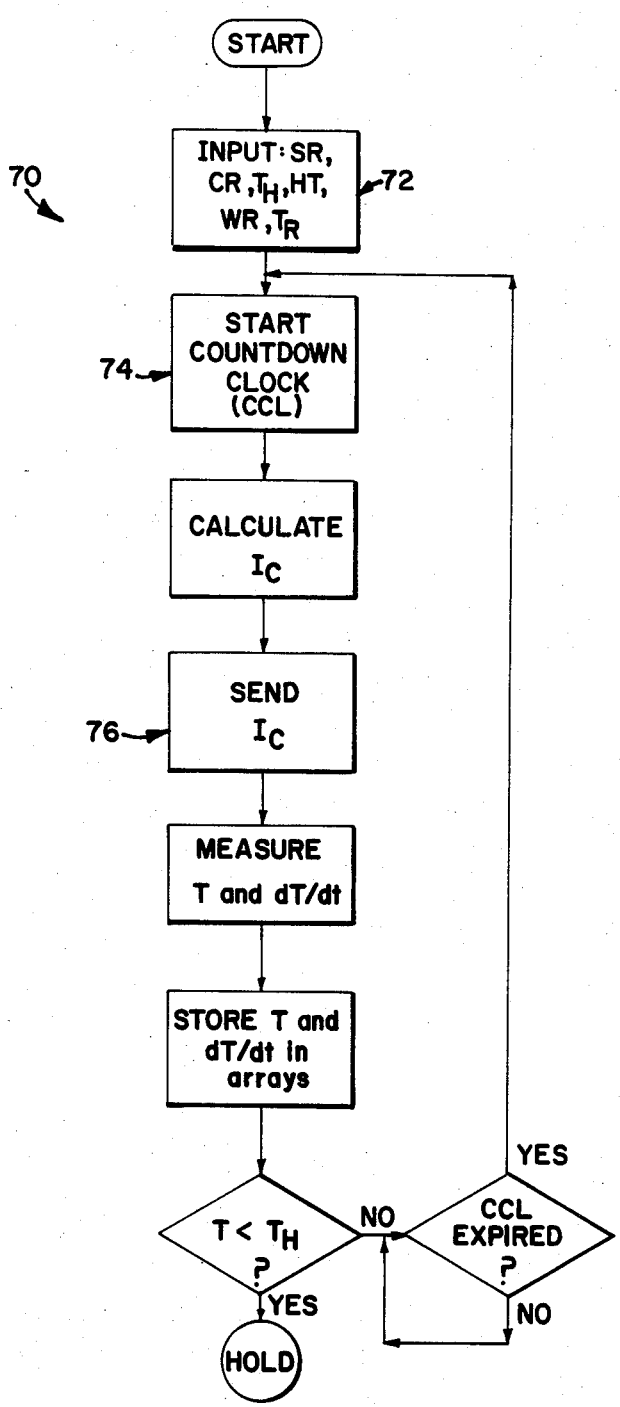
FIG. 7 shows a flow chart of a cooling routine for the computer of the device illustrated in FIG. 3.

FIG. 7 shows a flow chart for the cooling portion of the computer program, designated generally as 70. At the beginning of the test at the block denoted 72, the individual running the test has the opportunity to choose the "scan rate" (SR), "cooling rate" (CR), "holding temperature" ($T_H$), "holding time" (HT), "warming rate" (WR), and "warming temperature" ($T_R$). The scan rate is the rate at which the temperature, t, and rate of change of temperature, dT/dt, are sampled by the computer 22. The remaining terms are sufficiently self-explanatory. If the operator abstains from selecting particular parameters, the computer 22 will operate using typical default values stored therein.

Once the computer 22 is supplied with test parameters, it starts the freezing point test. A countdown clock is initiated at block 74 in the flow chart, the amount of time initially on the clock being determined by the scan rate discussed above. This clock will count down as further processing occurs.

Following initiation of the scan rate or countdown clock, the amount of cooling current required is calculated based on the specified cooling rate. The general method by which the amount of current is calculated is explained with reference to calculating the rewarming current and the procedure for calculating the cooling current is analogous. As shown in block 76, the programmable power supply 14 to cause it to produce the requisite current. The result of a computer program written according to the cooling cycle flow chart described above and "run" in the computer 22 is the cooling current vs. time plot shown in FIG. 5. A smooth, non-linear increase in cooling current is produced by the programmable power supply 14, and this non-linear increase in cooling current actually causes a linear decrease in temperature of the sample during periods of time that the sample is not undergoing a latent heat process. Such use of a thermoelectric cooling element is well known in the art and need not be described in further detail herein.

The central processor is next commanded by the computer program to measure the temperature and rate of change of temperature of the substance under test, a process of simply polling a pair of analog-to-digital converters on the analog interface board of the computer 22.

Finally, if the measured temperature is less than the holding temperature, e.g., $-60°$ Centigrade, the holding phase of the program is entered; otherwise, assuming that the countdown clock has expired, the loop is reentered and the cooling steps are once again step-wise completed.

Figure 8:
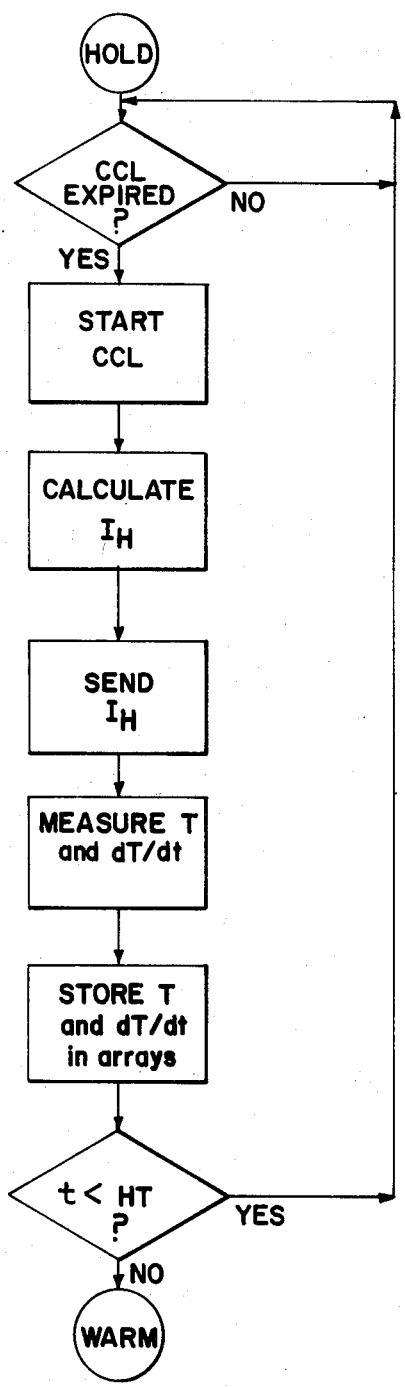
FIG. 8 shows a flow chart of a temperature-holding routine for the computer of the device illustrated in FIG. 3.

The "holding" flow chart, shown in FIG. 8, is very similar to the logic discussed with reference to the cooling flow chart, one difference being the location of the countdown clock decision diamond. The current is held constant during the holding period; thus, a constant analog voltage signal is sent to the programmable power supply 14 by the computer 22, as shown in FIG. 5 (the current produced by power supply 14 being directly porportional to the control voltage produced by computer 22). The temperature and rate of change of temperature of the substance are collected throughout the holding period. If the holding time elapses, the loop is exited and rewarming begins.

Figure 9:
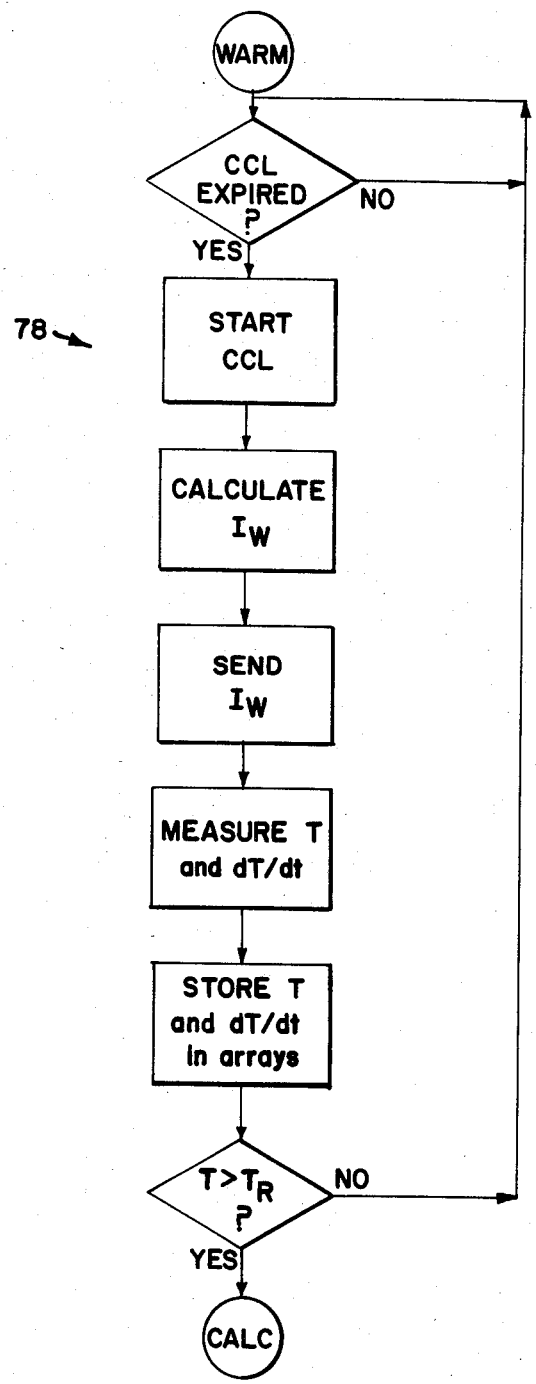
FIG. 9 shows a flow chart of a warming routine for the computer of the device illustrated in FIG. 3.

The warming, or rewarming, procedure is outlined in FIG. 9 and is generally designated with the reference numeral 78. Warming current is calculated by the computer 22 based on the running time and the preselected warming rate in the following way, for a preferred embodiment of a freezing point determination device constructed according to the principles of the present invention: if I is the current in amps; t is the running time in seconds; R is the preselected linear rewarming rate in degrees Centigrade per minute; and $D_r$, D and x are dummy variables, the following equations are used:

$$D_r = 50 + R/0.15$$

$$D = 2D_r + 550 + (D_r + 550)(x + x^2/4.05)$$

where $x = D_r t/17,500$ $$I = 0.91 + (-200)5.04/700$$

Deriving such equations for the particular device and substances under test is a straight-forward procedure for those skilled in the art, clearly well known to those skilled in the art of heat-transfer design and thermoelectric systems. If the temperature exceeds the warming or final temperature, $T_r$, the thermoelectric modules 56 are shut off and the calculation portion of the program is entered.

Figure 10:
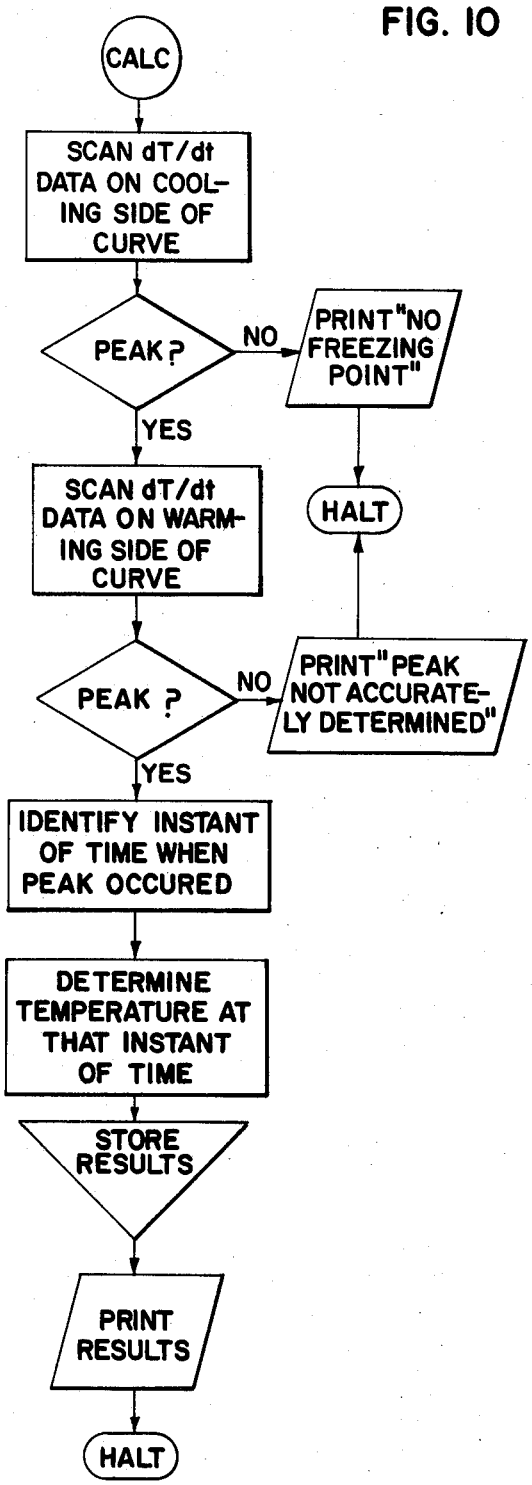
FIG. 10 shows a flow chart of a freezing point calculation routine for the computer of the device illustrated in FIG. 3.

A procedure for calculating the freezing point of the substance under test is flow charted in FIG. 10. The dT/dt data collected during cooling is automatically searched by the computer 22 for a peak rate of change of temperature. If a peak is not located a "thermal event" (freezing) did not occur, and "NO FREEZING POINT" or the like is printed prior to halting the computer.

If a peak dT/dt is located in the cooling data, the computer scans the warming data, once again searching for a peak rate of change of temperature. If a peak is located, the corresponding temperature (a temperature that existed at the instant of time that the peak rate of change of temperature occurred) is ear-marked as the freezing point of the substance and is stored and displayed prior to halting the freezing point determination device 10. It should be particularly noted that the computer 22, under program control, ignores the transition between holding temperature and rewarming, since this rapid transition creates a very large rate of increase of temperature but is not generally indicative of the freezing point of the substance.

It should be reemphasized that linear rewarming is advantageous, particularly for the analysis of mixtures, over exponential or other rewarming rates for at least three reasons: the error caused by excessive warming rates is avoided; the peak dT/dt is detectable using standard electronic techniques (since the rewarming rate is not excessively small at any point in the rewarming process); and the test consumes a reasonably small amount of time.

Although specific characteristics and advantages of the invention have been set forth in this description, it will be understood that the disclosure is, in many respects, only illustrative. Changes can be made in other details, particularly in matters of shape, size, arrangement of parts, type of electronic components, type of controller, etc., without exceeding the scope of the invention. The invention's scope is, of course, defined by the language in which the appended claims are expressed.

I claim:

1. A method for determining the freezing point of a mixture having an anticipated freezing point, comprising the following steps:
   (a) cooling the mixture to a temperature less than its anticipated freezing point;
   (b) controllably warming the mixture by actively controlling a net heat transfer thereto to increase the temperature of the mixture at a substantially constant rate during that time when the mixture is not undergoing a phase change;
   (c) identifying an instant of time when a peak rate of increase of temperature of the mixture occurs; and
   (d) determining the temperature of the mixture that existed at said instant of time, wherein this temperature is substantially equal to the freezing point of the mixture, wherein said substantially constant rate of increase of temperature is selected such that regardless of the freezing point of the mixture said rate of increase of temperature is sufficiently high to render identifiable said instant of time and is sufficiently low to provide acceptable accuracy.

2. The method in accordance with claim 1, wherein the mixture is thermoelectrically warmed during said warming step.

3. The method in accordance with claim 2, wherein the mixture is thermoelectrically cooled to a temperature less than its anticipated freezing point during said cooling step.

4. The method in accordance with claim 3, wherein said identifying step comprises:
   (a) measuring the temperature of the mixture during said warming step;
   (b) determining a rate of increase of temperature of the mixture during said warming step; and
   (c) identifying said peak rate of increase of temperature of the mixture that occurs during said warming step.

5. The method in accordance with claim 1, wherein the mixture is a hydrocarbon mixture and said constant rate is between approximately 20 and 25 degrees centigrade per minute.

6. The method in accordance with claim 5, wherein the hydrocarbon mixture is thermoelectrically warmed during said warming step.

7. The method in accordance with claim 6, wherein the hydrocarbon mixture is thermoelectrically cooled to a temperature less than its anticipated freezing point during said cooling step.

8. The method in accordance with claim 7, wherein said identifying step comprises:
   (a) measuring the temperature of the hydrocarbon mixture during said warming step;
   (b) determining a rate of increase of temperature of the hydrocarbon mixture during said warming step; and
   (c) identifying said peak rate of increase of temperature of the hydrocarbon mixture that occurs during said warming step.

9. The method in accordance with claim 1, further comprising the following step between said cooling and warming steps: maintaining the temperature of the mixture substantially constant for a predetermined period of time.

10. The method in accordance with claim 9, wherein the mixture is thermoelectrically warmed during said warming step.

11. The method in accordance with claim 10, wherein the mixture is thermoelectrically cooled to a temperature less than its anticipated freezing point during said cooling step.

12. The method in accordance with claim 11, wherein said identifying step comprises:
   (a) measuring the temperature of the mixture during said warming step;
   (b) determining a rate of increase of temperature of the mixture during said warming step; and
   (c) identifying said peak rate of increase of temperature of the mixture that occurs during said warming step.

13. The method in accordance with claim 5, further comprising the following step between said cooling and warming steps: maintaining the temperature of the hydrocarbon mixture substantially constant for a predetermined period of time.

14. The method in accordance with claim 13, wherein the hydrocarbon mixture is thermoelectrically warmed during said warming step.

15. The method in accordance with claim 14, wherein the hydrocarbon mixture is thermoelectrically cooled to a temperature less than its anticipated freezing point during said cooling step.

16. The method in accordance with claim 15, wherein said identifying step comprises:
   (a) measuring the temperature of the hydrocarbon mixture during said warming step;
   (b) determining a rate of increase of temperature of the hydrocarbon mixture during said warming step; and
   (c) identifying said peak rate of increase of temperature of the hydrocarbon mixture that occurs during said warming step.

17. A method for determining the freezing point of a hydrocarbon mixture having an anticipated freezing point, comprising the following steps:
   (a) thermoelectrically cooling the hydrocarbon mixture to a temperature less than its anticipated freezing point;
   (b) stabilizing the hydrocarbon mixture by maintaining the temperature of the cooled hydrocarbon mixture substantially constant for a predetermined period of time;
   (c) thermoelectrically warming the cooled hydrocarbon mixture by actively controlling a net heat transfer thereto to increase the temperature of the hydrocarbon mixture at a rate between approximately 20 and 25 degrees centigrade per minute during that time when the hydrocarbon mixture is not undergoing a phase change;
   (d) measuring the temperature of the hydrocarbon mixture during said warming step;
   (e) determining a rate of increase of temperature of the hydrocarbon mixture during said warming step;
   (f) identifying a peak rate of increase of temperature of the hydrocarbon mixture that occurs during said warming step;
   (g) identifying an instant of time when said peak rate of increase of temperature of the hydrocarbon mixture occured; and
   (h) determining the temperature of the hydrocarbon mixture that existed at said instant of time, wherein this temperature is substantially equal to the freezing point of the hydrocarbon mixture, wherein said rate of increase of temperature is selected such that regardless of the freezing point of the mixture said rate of increase of temperature is sufficiently high to render identifiable said instant of time and is sufficiently low to provide acceptable accuracy.

18. The method in accordance with claim 17, wherein said temperature measuring step comprises placing a temperature transducer in thermal communication with the hydrocarbon mixture, said temperature transducer having an electrical transducer output signal representative of the temperature of the hydrocarbon mixture and wherein said rate determining step comprises electronically differentiating said transducer output signal with respect to time to generate an electrical differentiator output signal.

19. The method in accordance with claim 18, wherein said peak identifying step comprises electronically analyzing said differentiator output signal to locate said peak rate of increase of temperature of the hydrocarbon mixture.

20. The method in accordance with claim 19, wherein the hydrocarbon mixture is an aviation fuel.

21. A device for determining the freezing point of a mixture having an anticipated freezing point, comprising:
   (a) means for cooling the mixture to a temperature less than its anticipated freezing point, said cooling means being in thermal communication with the mixture;
   (b) means for controllably warming the mixture by actively controlling a net heat transfer thereto to increase the temperature of the mixture at a substantially constant rate during that time when the mixture is not undergoing a phase change, said warming means being in thermal communication with the mixture;
   (c) means for measuring the temperature of the mixture, said temperature measuring means being in operative proximity of the mixture;
   (d) rate sensing means operatively disposed to monitor the mixture for providing a rate signal indicative of the rate of change of temperature of the mixture; and
   (e) means operatively connected to said temperature measuring means and to said rate sensing means for determining an instant of time when said rate of increase of temperature attains a maximum and for providing a freezing point test output signal indicative of the temperature of the mixture at said instant of time, wherein this temperature is substantially equal to the freezing point of the mixture, wherein said substantially constant rate of increase of temperature is selected such that regardless of the freezing point of the mixture said rate of increase of temperature is sufficiently high to render identifiable said instant of time and is sufficiently low to provide acceptable accuracy.

22. The device in accordance with claim 21, wherein said warming means comprises means for thermoelectrically warming the mixture.

23. The device in accordance with claim 22, wherein said cooling means comprises means for thermoelectrically cooling the mixture.

24. The device in accordance with claim 23, wherein said temperature measuring means provides a first temperature signal and a second temperature signal, said temperature signals being indicative of the temperature of the mixture; and said first temperature signal is received by said rate sensing means and said second temperature signal is received by said instant of time determining means.

25. The device in accordance with claim 24, wherein said first and second temperature signals are of analog nature and said rate sensing means comprises an analog time differentiation circuit.

26. The device in accordance with claim 25, wherein said instant of time determining means comprises a digital computer.

27. The device in accordance with claim 26, wherein said temperature measuring means comprises a thermocouple.

28. The device in accordance with claim 21, wherein the mixture is a hydrocarbon mixture and said constant rate is between approximately 20 and 25 degrees centigrade per minute.

29. The device in accordance with claim 28, wherein said warming means comprises means for thermoelectrically warming the hydrocarbon mixture.

30. The device in accordance with claim 29, wherein said cooling means comprises means for thermoelectrically cooling the hydrocarbon mixture.

31. The device in accordance with claim 30, wherein said temperature measuring means provides a first temperature signal and a second temperature signal, said temperature signals being indicative of the temperature of the hydrocarbon mixture; and said first temperature signal is received by said rate sensing means and said second temperature signal is received by said instant of time determining means.

32. The device in accordance with claim 31, wherein said first and second temperature signals are of analog nature and said rate sensing means comprises an analog time differentiation circuit.

33. The device in accordance with claim 32, wherein said instant of time determining means comprises a digital computer.

34. The device in accordance with claim 33, wherein said temperature measuring means comprises a thermocouple.

35. The device in accordance with claim 21, further comprising means for maintaining the temperature of the mixture substantially constant for a predetermined period of time at a temperature less than its anticipated freezing point, said maintaining means being in thermal communication with the mixture.

36. The device in accordance with claim 35, wherein said warming means comprises means for thermoelectrically warming the mixture.

37. The device in accordance with claim 36, wherein said cooling means comprises means for thermoelectrically cooling the mixture.

38. The device in accordance with claim 37, wherein said temperature measuring means provides a first temperature signal and a second temperature signal, said temperature signals being indicative of the temperature of the mixture; and said first temperature signal is received by said rate sensing means and said second temperature signal is received by said instant of time determining means.

39. The device in accordance with claim 38, wherein said first and second temperature signals are of analog nature and said rate sensing means comprises an analog time differentiation circuit.

40. The device in accordance with claim 39, wherein said instant of time determining means comprises a digital computer.

41. The device in accordance with claim 40, wherein said temperature measuring means comprises a thermocouple.

42. The device in accordance with claim 28, further comprising means for maintaining the temperature of the hydrocarbon mixture substantially constant for a predetermined period of time at a temperature less than its anticipated freezing point, said holding means being in thermal communication with the hydrocarbon mixture.

43. The device in accordance with claim 42, wherein sid warming means comprises means for thermoelectrically warming the hydrocarbon mixture.

44. The device in accordance with claim 43, wherein said cooling means comprises means for thermoelectrically cooling the hydrocarbon mixture.

45. The device in accordance with claim 44, wherein said temperature measuring means provides a first temperature signal and a second temperature signal, said temperature signals being indicative of the temperature of the hydrocarbon mixture; and said first temperature signal is received by said rate sensing means and said second temperature signal is received by said instant of time determining means.

46. The device in accordance with claim 45, wherein said first and second temperature signals are of analog nature and said rate sensing means comprises an analog time differentiation circuit.

47. The device in accordance with claim 46, wherein said instant of time determining means comprises a digital computer.

48. The device in accordance with claim 47, wherein said temperature measuring means comprises a thermocouple.

49. A device for measuring the freezing point of a hydrocarbon mixture having an anticipated freezing point, comprising:
  (a) thermoelectrical means for cooling the hydrocarbon mixture to a cool temperature less than its anticipated freezing point, said cooling means being in heat conductive engagement with the hydrocarbon mixture;
  (b) thermoelectrical means for maintaining the hydrocarbon mixture at said cool temperature for a predetermined period of time to stabilize the hydrocarbon mixture, said thermoelectrical maintaining means being in heat conductive engagement with the hydrocarbon mixture;
  (c) thermoelectrical means for controllably warming the hydrocarbon mixture by actively controlling the net heat transfer thereto to increase the temperature of the hydrocarbon mixture from said cool temperature to a warm temperature at a rate of approximately 20 to 25 degrees centigrade per minute during that time when the hydrocarbon mixture is not undergoing a phase change, said thermoelectrical warming means being in heat conductive engagement with the hydrocarbon mixture;
  (d) a thermocouple in heat conductive engagement with the hydrocarbon mixture, said thermocouple providing a first thermocouple output signal and a second thermocouple output signal;
  (e) differentiation means for providing a rate signal indicative of the rate of change of temperature of the hydrocarbon mixture as it is being warmed, said differentiation means receiving said first thermocouple output signal; and
  (f) a digital computer adapted to receive said second thermocouple output signal and said rate signal, said digital computer determining an instant of time when the rate of increase of temperature obtains a maximum and providing a freezing point test output signal indicative of the temperature of the hydrocarbon mixture at said instant of time, wherein this temperature is substantially equal to the freezing point of the mixture, wherein said rate of increase of temperature is selected such that regardless of the freezing point of the mixture said rate of increase of temperature is sufficiently high to render identifiable said instant of time and is sufficiently low to provide acceptable accuracy.

50. The device in accordance with claim 49, wherein said hydrocarbon mixture is an aviation fuel.

* * * * *